Figure 1:
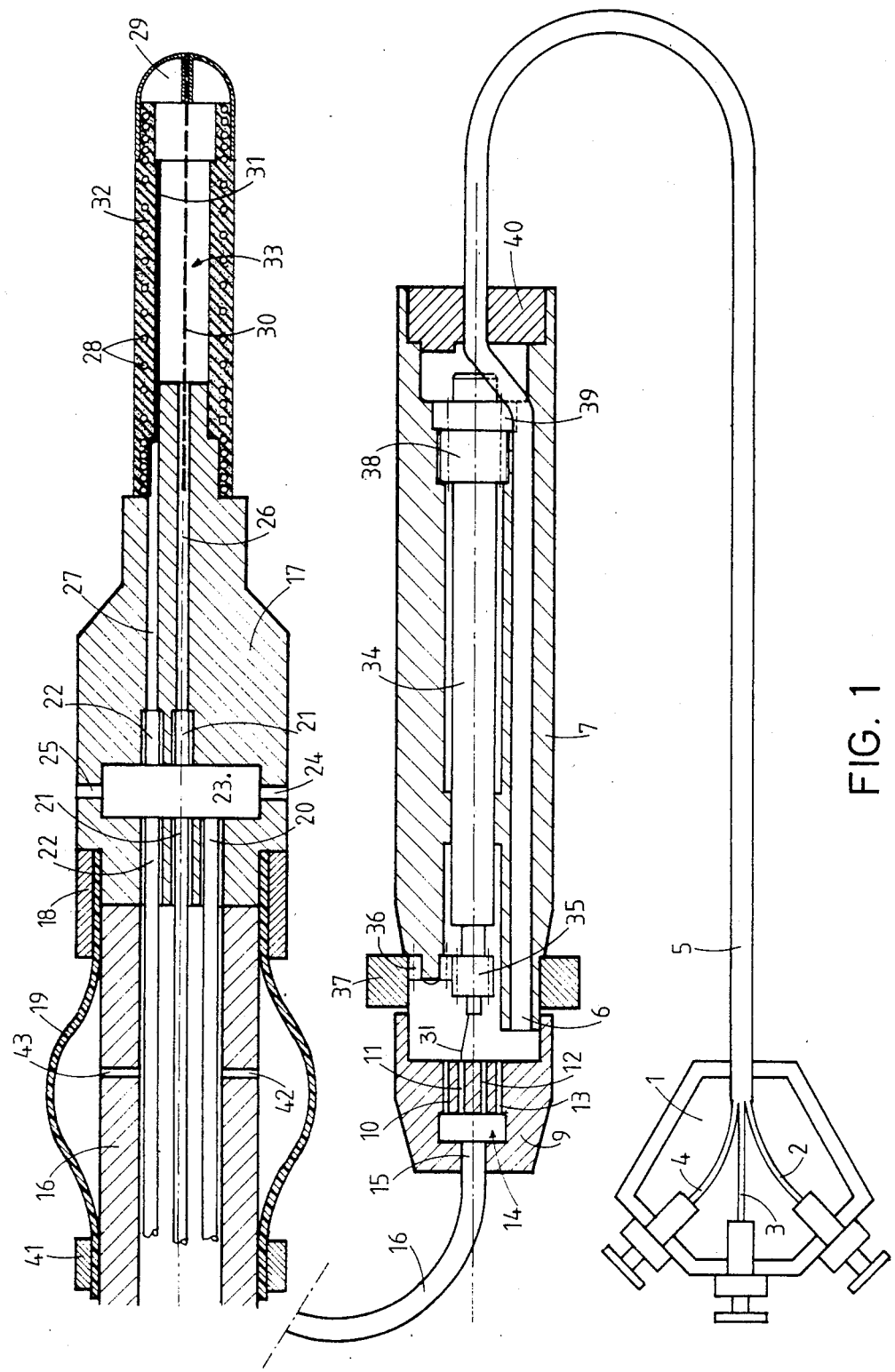

United States Patent [19]

Bonello et al.

[11] Patent Number: 4,650,467
[45] Date of Patent: Mar. 17, 1987

[54] REMOTE CONTROL CATHETER

[75] Inventors: Philippe Bonello, Grand-Saconnex; Maurice Jeanmonod, Meyrin, both of Switzerland

[73] Assignee: Sarcem S.A., Meyrin, Switzerland

[21] Appl. No.: 768,335

[22] Filed: Aug. 22, 1985

[30] Foreign Application Priority Data

Aug. 22, 1984 [CH] Switzerland ............... 4010/84

[51] Int. Cl.⁴ ............................................ A61M 25/00
[52] U.S. Cl. ............................................ 604/95; 128/8; 128/348.1
[58] Field of Search ........................................ 128/6–8, 128/344, 348.1, 656–658, 772; 604/95–103, 280–283

[56] References Cited

U.S. PATENT DOCUMENTS

| | | | |
|---|---|---|---|
| 2,211,975 | 8/1940 | Hendrickson | 604/282 |
| 2,498,692 | 2/1950 | Mains | 604/95 |
| 3,416,531 | 12/1968 | Edwards | 604/95 |
| 3,470,876 | 10/1969 | Barchilon | 604/95 |
| 4,248,234 | 2/1981 | Assenza et al. | 604/282 X |
| 4,561,439 | 12/1985 | Bishop et al. | 128/348.1 |
| 4,582,181 | 4/1986 | Samson | 604/95 X |
| 4,586,923 | 5/1986 | Gould et al. | 604/95 |

FOREIGN PATENT DOCUMENTS

| | | | |
|---|---|---|---|
| 129955 | 10/1932 | Austria | 128/8 |
| 43-27685 | 11/1968 | Japan | 604/95 |

Primary Examiner—Dalton L. Truluck
Attorney, Agent, or Firm—Young & Thompson

[57] ABSTRACT

The present invention is a remote control catheter designed principally for cardio-vascular surgery, characterized by the fact that it permits its user to directly control, starting from the handle of the instrument, the orientation of its head by means of a control wire (31) attached to the extremity of the heat of the catheter while at the same time being eccentric with respect to the axis of this latter on the one hand, and to the extremity of the traction pinion (34) placed at the interior of the handle on the other hand, this latter being displaceable in the direction of its axis and consequently to pull or release the control wire (31) while the user exerts a rotary movement to the control collar (37) driving through its interior teeth the intermediate pinion (36) this latter meshing at its exterior in the tooth (35) of the traction pinion (34) which similarly has a male screw threading (38) cooperating with a female screw threading (39) fixed with respect to the handle.

9 Claims, 1 Drawing Figure

REMOTE CONTROL CATHETER

The present invention has for an object a catheter with a head that is adjustable by remote control, the principal applications of which are to be situated at the location of cardio-vascular illnesses of the coronary arteries, characterized by the fact that it permits its user to reach without difficulty through multiple circulatory branchings the zone to be treated, while having the possibility to cause by remote control the stiffening of its head at the required time, at no matter what moment during the surgical operation.

The accompanying drawings shows by way of non-limiting example, an embodiment of the object of the present invention.

FIG. 1 is a general view in cross section.

The remote control catheter shown in the drawing comprises a supply source 1 having three tubes 2, 3 and 4 joined together in a casing 5 of which the one of its extremities is fixed to the outlet of the supply source 1 while the second extremity coincides with the end of the cylindrical bore 6 effected in the housing 7 of the handle of the catheter.

At the three tubes 2, 3 and 4 is formed, approximately abreast of the exit of the cylindrical bore 6, a supplementary tube 8. The head 9 of the handle will then have four channels 10, 11, 12 and 13 terminating at the inlet of the chamber 14 and designed to position and fix by fastening the four tubes 2, 3, 4 and 8. In between the chamber 14 and the extremity of the head 9 of the handle is provided a fifth channel 15 of greater diameter, the role of which is to position and to fix similarly by fastening the extremity of a casing 16 containing the tubes 8, 2 and 3, the tube 4 terminating at the inlet of the chamber 14.

At the other extremity of the casing 16 and in its immediate extension the support 17 for the head of the catheter is fixed by means of the fastening collar 18 covering the two elements, the second function of which is to position rigidly and at the same time the one of the two extreme portions of the vesicle 19 on the casing 16 and the support 17 while assuring between the casing 16 and the support 17 on the one hand and the vesicle 19 on the other hand the tightness necessary for the proper functioning of the instrument.

In examining the support 17 of the catheter head, it will be noted that this latter possesses three channels 20, 21 and 22 designed to position and to fix by fastening the three tubes 8, 2 and 3, and opening into a distribution chamber 23 extending to two lateral openings 24 and 25 opening upon the exterior. Only the channels 21 and 22 going beyond the chamber 23 are extended in two channels of smaller diameter numbered 26 and 27.

With respect to the catheter head itself, this latter is composed of a cylindrical spring 28 the base of which is overlapped on the support 17, a rounded end 29 of which the circular shank overlaps on the other extremity of the spring 28, a wire 30 in the form of an inverted U shown in the drawing in dashed line seated in the slit effected in the head of the rounded end 29 and welded at its two extremities to the base of the spring 28, a control wire 31 soldered at its extremity to the circular shank of the rounded end 29, this control wire being eccentric with respect to the axis of this latter, all molded in a rubber-like material so as to obtain a chamber 33 the role of which is to be able to contain a fluid under a certain pressure.

To direct the head of the catheter initially to the one or the other of the chosen circulatory branchings, the user prepares to actuate his instrument having three degrees of freedom.

Advance or retraction of the assembly and therefore of its head, rotation of the assembly about itself in one direction or the other with respect to its axis, inclination of the head solely by virtue of the force of traction that the user will exert on the control wire 31 encased by the tube 8, the wire 31 being attached at its extremity to that of the traction axle 34 possessing a toothed portion 35 engaged with an intermediate gear 36 itself engaged in its rotation with the interior teeth of the control sleeve 37 directly accessible to the user.

So that the traction axle 34 retracts when the user exerts a rotation movement on the control sleeve 37, it is necessary that this axle 34 have a threading 38 engaging in a fixed threading 39, the two principal functions of the stopper 40 being to play the role of the stop of the axle 34 on the one hand and to maintain the casing 5 centered and in place on the other hand.

If the stiffening of the catheter head already exists and in a very weak measure by the equilibrium established between the intrinsic force of the cylindrical spring 28 and the traction force exerted on the control wire 31, it is possible to amplify this stiffening by injecting through the tube 3 under a certain pressure, a fluid to the interior of the chamber 33 of which the windings of the cylindrical spring 28 form a brace to the lateral forces developed by the fluid, the wire 30 in the form of an inverted U constituting at its contour a brace to the longitudinal forces, impeding an elongation of the chamber 33 and in turn of the head of the catheter. On the other hand, and for the best inclination movement of the head, the plane formed by the wire 30 and the plane formed by the control wire 31 with the axis of the cylindrical spring 28 will be orthogonal with respect to one another.

As to the balloon inflatable by means of a gas for the conventional and well known catheters, this function, of which the therapeutic end is the same, is replaced in the instrument of the present invention by a type of vesicle 19 inflatable by means of a fluid introduced through the tube 4 and penetrating into the casing 16 being able to be, in the event of a contrasting liquid, practically incompressible further permitting immediate controls to be read easily in radioscopic examinations.

By other means and in case of leakage, the harmlessness of the contrasting liquid must be considered as a criterion of the greatest importance. Needless to say, the necessary tightness between the other extreme portion of the vesicle 19 and the casing 16 is assured according to the principle already described by a second fastening collar 41.

The liquid necessary for the filling of the vesicle 19 is injected through the tube 4, totally overrunning the chamber 14 so as to be introduced next in the casing 16 between the tubes 2, 3 and 8 to escape finally through the lateral opening 42 and 43 effected on this casing 16 and situated substantially at midlength of the vesicle 19.

There remains the conventional and well known function consisting of introducing the contrasting liquid to the interior of the considered circulatory branching for the purpose of marking for reading in radioscopic examinations. To that end, the contrasting liquid is injected through the tube 2 overrunning the chamber 23 and escaping to the exterior in the branching through the two openings 24 and 25 of the present catheter.

We claim:

1. Remote control catheter comprising a head having a support, a handle having a control device, and a casing unit connecting said head and said handle, said head comprising a hollow, flexible, cylindrical finger substantially aligned with said support; and a flexible tensioning element having first and second extremities, extending from the handle to the head of the catheter and passing through the interior of the casing, said first extremity of said tensioning element being eccentrically disposed throughout said cylindrical finger of the head of the catheter, and the said second extremity being fixed to the handle of the catheter, whereby a traction forced exerted on said tensioning element will bend said finger; said flexible finger comprising a cylindrical helical spring coaxially embedded in said finger and substantially coextensive with said finger, said spring comprising at least a middle portion having coils which are each separated from the others in rest position, whereby when said traction force is released on said tensioning element said finger automatically resumes a straight rest position.

2. Catheter according to claim 1, wherein said cylindrical helical spring has first and second extremities, said second extremity being interfitted with the said support for the head of the catheter.

3. Catheter according to claim 2, wherein said cylindrical finger comprises a rounded end having connecting means, said first extremity of said cylindrical helical spring being interfitted with said connecting means of said rounded end.

4. Catheter according to claim 1, wherein said catheter handle comprises a tensioning shaft disposed in its interior, to which said tensioning shaft said second extremity of said tensioning element is fixed; said tensioning shaft comprising a toothed gear engaged with an interiorly toothed gear ring disposed on said catheter handle, and further comprising male screw threading cooperating with female screw threading fixed on the interior of said handle, whereby rotation of said gear ring will cause axial displacement of said tensioning shaft.

5. Catheter according to claim 1, wherein said finger comprises a closed distal end, and said catheter comprises means for supplying a fluid under pressure to said finger, so as to cause stiffening of the said finger.

6. Catheter according to claim 5, wherein said finger comprises a U-shaped wire encased in said finger and extending longitudinally of said finger across said distal end.

7. Catheter according to claim 6, wherein the axis of said tensioning element and the axis of said cylindrical finger define a first plane, and said U-shaped wire defines a second plane, said first and second planes being orthogonal to one another.

8. Catheter according to claim 1, and a vesicle inflatable by means of a liquid, preferably a contrast liquid, said vesicle being fixed to said support of the catheter head.

9. Catheter according to claim 8, wherein said vesicle comprises proximal and distal ends both fixed to said catheter head support by means of fastening collars, and said cathether head support comprises radial openings in an intermediate region of said vesicle, for introducing a contrast liquid into said vesicle.

* * * * *